United States Patent [19]

Mabuchi et al.

[11] 4,182,919

[45] Jan. 8, 1980

[54] PROCESS FOR REACTION IN CATALYST SUSPENSION SYSTEM

[75] Inventors: Shunsuke Mabuchi; Sadakatsu Kumoi; Kenji Tsuzuki, all of Shin-nanyo, Japan

[73] Assignee: Toyo Soda Manufacturing Co., Ltd., Yamaguchi, Japan

[21] Appl. No.: 887,217

[22] Filed: Mar. 16, 1978

[30] Foreign Application Priority Data

Mar. 31, 1977 [JP] Japan .................................. 52-35234

[51] Int. Cl.² ...................... C07C 31/20; C07C 87/00; C07C 59/10; C07C 67/05
[52] U.S. Cl. ................................... 568/861; 560/244; 562/531; 260/563 R; 260/580; 568/863; 260/687 R; 260/690
[58] Field of Search .............. 23/288 E; 568/861, 863; 560/244; 562/531; 260/580, 563 C

[56] References Cited

U.S. PATENT DOCUMENTS

| 2,879,306 | 3/1959 | Hutchinson | 568/861 |
|---|---|---|---|
| 3,449,445 | 6/1969 | Wetherill | 568/861 |
| 3,484,214 | 12/1969 | Gehring et al. | 23/288 E |
| 3,829,478 | 8/1974 | Ohorodnik et al. | 23/288 E |
| 3,847,989 | 11/1974 | Platz et al. | 568/861 |

FOREIGN PATENT DOCUMENTS 45-20884  7/1970  Japan ................................... 23/288 E

*Primary Examiner*—Joseph E. Evans
*Attorney, Agent, or Firm*—Oblon, Fisher, Spivak, McClelland & Maier

[57] ABSTRACT

A reaction in a catalyst suspension system is carried out by using a reactor equipped with a filter for separating the catalyst in the reactor.

13 Claims, No Drawings

PROCESS FOR REACTION IN CATALYST SUSPENSION SYSTEM

BACKGROUND OF THE INVENTION

FIELD OF THE INVENTION

The present invention relates to a continuous reaction in catalyst suspension system in liquid phase by using a reactor equipped with a filter in the reactor whereby the reaction mixture from which the catalyst is separated, is continuously discharged through the filter.

DESCRIPTION OF THE PRIOR ART:

In chemical industries, a fixed bed system using a solid catalyst has been widely employed for hydrogenations. For example, in the hydrogenation such as a production of aniline from nitrobenzene, a production of cyclohexane from benzene and a hydrogenation of a distilled oil in the petroleum refining industry, a gaseous phase fixed bed system has been employed. In a desulfurization of heavy oil by hydrogenation, a liquid phase fixed bed system has been employed.

In these fixed bed system, a separation of a catalyst from the reaction mixture is easily attained and a catalyst separator is not required and the reaction can be attained in the presence of high ratio of a catalyst, advantageously.

However, a pellet form catalyst or a large particle size catalyst is used in the fixed bed system, the deterioration of the surface of the catalyst is remarkably caused to be low coefficient of the catalyst in a reaction causing the poisoning of the catalyst.

For example, the fixed bed system is not preferably employed in a hydrogenation of an organic peroxide, because of the following reason.

In the hydrogenation of an organic peroxide, the poisoning of the catalyst is remarkably severe whereby, it is necessary to maintain the equilibrium of the poisoning and the reactivation of the catalyst to the side of the reactivation so as to use the catalyst in highly active condition. Accordingly, it is necessary to carry out the hydrogenation in the catalyst system having high content of the catalyst to the organic peroxide and it is also necessary to impart high effect for contacting hydrogen gas, the reaction mixture and the solid catalyst. From the viewpoints, it is optimum to employ a reaction system suspending powdery catalyst having large specific surface area in the reaction mixture at high concentration The hydrogenation of the organic peroxide is a severe exothermic reaction. Accordingly, when the fixed bed system is employed for the hydrogenation, it is not easy to cool it whereby a local abnormal reaction caused by hot spots may be resulted to cause serious parmanent poisoning of the catalyst. It is difficult to maintain high catalytic activity for a long time.

From these viewpoints, a fluidized bed system of a catalyst suspension is considered to be optimum for an industrial hydrogenation of an organic peroxide.

As the hydrogenation in a fluidized bed system of a catalyst suspension, the hydrogenation of an alkyl anthroquinone in the production of hydrogen peroxide or the hydrogenation of glucose to sorbitol etc. have been known.

In the fluidized bed system of a catalyst suspension, a powdery catalyst can be used whereby the effect for contacting gas-liquid-solid phases is advantageously high. However, the system requires a filter for separating the catalyst from the reaction mixture. Moreover, the operation for recycling the catalyst to a reactor for the reuse of the catalyst has been disadvantageously required.

In a reaction using low concentration of a catalyst, the load for the operation of the separation and the reuse of the catalyst is rather small because of small amount of the catalyst. However, in a reaction using high concentration of a catalyst, the equipments for the separation, the recovery and the reuse of the catalyst are disadvantageously required at high portion because of large amount of the catalyst.

It has been known as the reaction in the fluidized bed system of a catalyst suspension in liquid phase which does not require a catalyst separator, the production of cyclohexane from benzene by I.F.P. method has been known.

In the reaction, cyclohexane produced in the fluidized system of a catalyst suspension is discharged in a gaseous phase from the top of the reactor whereby the catalyst is separated from the reaction product and the Raney nickel catalyst is remained in the reactor.

When the reaction product has a low boiling point as cyclohexane, the separation of the catalyst from the reaction product is easy. However, when the reaction product has a high boiling point and the reaction product should be discharged in a form of a liquid phase, as the hydrogenation of an organic peroxide especially the hydrogenation of polymeric butadiene peroxide to product butanediol, a separator for separating the catalyst from the reaction mixture is required.

In a reaction requiring high concentration of a catalyst such as the hydrogenation of an organic peroxide, the mixture of the catalyst and the reaction product discharged from the reactor should be separated and the slurry of the catalyst having high concentration which is separated and is not easily processsed should be recycled to the reactor. Accordingly, the catalyst recovery step requires remarkably complicated operation and troubles of a clogging of a pipe and a scaling etc. are found and a smooth operation of the apparatus is not easily attained. Moreover, a cost of power consumption required for the catalyst recovery is remarkably high.

The processes for the reaction in a fluidized bed system of a catalyst suspension at high concentration and the following flow of the catalyst for recovery and reuse have serious disadvantages in the operation.

SUMMARY OF THE INVENTION

It is an object of the present invention to overcome the difficulty in the fluidized bed system of a catalyst suspension.

It is another object of the present invention to provide a novel process in the suspension fluidized bed system of a catalyst suspension at high concentration wherein the catalyst is remained at high concentration in the reactor and only the reaction mixture solution is discharged from the reactor, and the complicated operation for recovery of the catalyst can be eliminated in the reaction in a heterogeneous liquid phase containing a solid catalyst.

The foregoing and other objects of the present invention have been attained by continuously carrying out a reaction and a separation of a catalyst in a fluidized bed system of a catalyst suspension at high concentration by using a reactor equipped with a filter for separating the catalyst in the reactor.

The reaction is preferably carried out by using the filter having a flexible filter medium equipped in the reactor to maintain stable filtering speed for a long time.

DETAILED DESCRIPTION OF THE PREFERRED EMBODIMENTS

The process of the present invention can be applied for various reactions in a catalyst suspension such as hydrogenations and oxidations in a liquid phase as a catalyst suspension.

Hydrogenation (a) Sorbitol can be produced by a hydrogenation of glucose in the presence of a nickel catalyst supported on diatomaceous earth.

(b) Aniline can be produced by a hydrogenation of nitrobenzene in the presence of copper catalyst. Cyclohexylaniline can be produced by a hydrogenation of aniline in the presence of a catalyst of nickel or cobalt.

Oxidation (a) Diacetoxy butene can be produced by an oxidation of butadiene in the presence of a palladium catalyst supported on carbon in acetic acid.

(b) Gluconic acid can be produced by an oxidation of glucose in the presence of a palladium catalyst supported on carbon in water.

The process of the present invention is especially advantageous when a catalyst content (including a supporter) is more than 3 wt.% in the fluidized bed system.

In the process of the present invention, a filter is equipped in a reactor especially an autoclave. The level of the reaction mixture of the catalyst suspension is usually controlled by the position of the filter. The reaction mixture of the catalyst suspension is usually stirred so as to maintain the powdery catalyst in the form of the suspension under substantially preventing the excessive deposition of the powdery catalyst on the surface of the filter medium. The shape of the filter medium can be a bag, a cylinder, a spiral tube, and a plate and a receiver.

It is preferable to have the filter medium which prevent a deposition of the powdery catalyst in the catalyst suspension. A flexible filter medium is especially preferable for this purpose.

The detail of the process of the present invention will be further described.

As the embodiments, the hydrogenation of an organic peroxide in the presence of a nickel catalyst will be illustrated.

As a filter medium for a filter, a rigid material such as ceramics and sintered metals can be used. Even though the hydrogenation and the separation of the catalyst can be continuously and smoothly carried out by using the ceramic or the sintered metal as the filter medium. However, after a long reaction time the filtering speed is reduced.

In order to maintain enough filtering speed and to perform the reaction smoothly, it is necessary to carry out the backwashing of the filter.

When the rigid filter medium is used the effect for recovery of the filtering speed by the backwashing is relatively low. In order to continuously and smoothly perform the reaction for a long time, it is necessary to have a large filtering area of the filter in the reactor.

In the hydrogenation of the organic peroxide using the powdery sulfur resistant nickel catalyst, when a filter having a filter medium made of flexible stainless steel woven fabric is used, the decrease of the filtering speed during the reaction time is small and the period for the backwashing of the filter is relatively long and stable filtering speed could be maintained for a long time. Moreover, the effect of the recovery of the filtering speed by the backwashing of the filter can be large.

As the fact, in the present invention, it is advantageous to use a flexible filter medium as the effective filter medium in order to maintain high filtering speed.

The filter medium is always contacted with the reaction mixture whereby high chemical resistance to the chemicals at the reaction temperature is required. Accordingly, it is suitable to use stainless steel woven fabric and stainless steel gauze. It is also possible to use a flexible filter medium made of stainless steel, felt, stainless steel fiber and metallic woven fabric, gauze, felt and web sintered medium made of nickel, aluminum, etc. It is also possible to use the woven fabric made of a synthetic fiber such as nylon, vinyl type fiber, etc. It is preferable to use a filter medium having high pressure resistance, high wearing resistance and high mechanical strength.

In a reaction at relatively slow reaction velocity, that is, the reaction which can be carried out at relatively slow discharging velocity, it is possible to use a rigid filter medium such as ceramics and sintered metal.

In comparison with the case using a flexible filter medium, it is necessary to carry out backwashing operation for many times in relatively short period.

As the process of the backwashing, the backwashing with a liquid advantageously imparts superior recovery effect of the filtering speed in comparison with the backwashing with a gas.

The pressure difference required for imparting enough filtering speed, is dependent upon the volumetric contractivity of the catalyst, that is, the kind of the catalyst and it is usually less than 35 kg/cm$^2$ preferably less than 20 kg/cm$^2$. Even though the pressure difference is higher than 35 kg/cm$^2$, the filtering speed is not further improved.

The catalyst used in the reaction is preferably a catalyst which is easily filtered.

When the sulfur resistant nickel catalyst having a particle distribution of 1 to 80$\mu$, is used, a transparent reaction mixture which does not contain the catalyst can be discharged at stable filtering speed by using a flexible filtering medium.

When the other catalysts beside nickel catalyst are used, the filtering speed can be improved by supporting the catalytic component on a filter aid such as diatomaceous earth, carbon, etc.

In accordance with the present invention, the kind, particle size and supporter of the catalyst can be selected as desired advantageously.

Sometimes a small amount of a catalyst passed through a filter with the filtrate is discharged depending upon a kind and pore size of filter medium. A small amount of the catalyst is passed through the filter at the initiation of the reaction.

The catalyst discharged through the filter with the reaction mixture is treated and recovered by the following reaction mixture settling vessel or a catalyst separator.

Since the amount of the discharged catalyst is quite smaller than the total catalyst, the size of the catalyst separator can be small and the economical effect of the process is not reduced.

The concentration of the catalyst used in the reaction mixture is not limited. When the catalyst content is less than 3 wt.%, the reaction and the catalyst separation attained independently in the fluidized bed system of a catalyst suspension and the amount of the catalyst recovered and recycled is relatively small and a trouble is not so serious.

However, when the reaction requires more than 3 wt.% of the catalyst content as the reaction mechanism in the fluidized bed system of a catalyst suspension, the separation and the recovery and recycling of the catalyst are not easy.

In accordance with the process of the present invention, it is unnecessary to recycle the slurry having high catalyst concentration recovered in the catalyst separation step, to the reactor whereby remarkable advantages on the operation in the reaction and the utilities can be attained. Accordingly, the process of the present invention is remarkably advantageous.

The process of the present invention can be applied for the reaction under the atmospheric pressure as well as higher pressure. When the process of the present invention is applied for the reaction under higher pressure, the advantages are especially high.

When the reaction under higher pressure in the fluidized bed system containing high concentration of the catalyst is performed, it is unnecessary to recycle a large amount of the catalyst to an autoclave under high pressure and it is remarkably advantageous from the viewpoint of the operation and apparatus.

The process of the present invention can be applied for the liquid phase reaction in which solid-liquid or solid-liquid-gas are contacted. Thus, when the process of the present invention is applied for the heterogeneous liquid phase hydrogenation using high concentration of a catalyst for hydrogenation, excellent characteristics of the present invention is imparted.

In the reaction requiring high concentration of a catalyst for maintaining high catalytic activity for a long time such as the hydrogenation of a polymeric butadiene peroxide in the presence of a nickel catalyst, the continuous reaction can be attained by the application for the process of the present invention to attain various advantages.

Having generally described the invention, a more complete understanding can be obtained by reference to certain specific examples, which are included for purposes of illustration only and are not intended to be limiting unless otherwise specified.

EXAMPLE 1

Polymeric butadiene peroxide as the starting material for the hydrogenation used in the continuous hydrogenation was produced by the following conditions.

In a 2 liter autoclave made of a stainless steel (SUS-32) equipped with an electromagnetic stirrer, 1,3-butadiene was oxidized in a solvent of ethyl acetate at 90° C. under 1.8 kg/cm² of oxygen partial pressure with the mixture gas of 90% nitrogen and 10% oxygen to obtain a polymeric butadiene peroxide conversion of 30%. The unreacted butadiene was removed under a reduced pressure from the reaction mixture to obtain the polymeric butadiene peroxide. The product was used for the hydrogenation.

In a 1 liter autoclave made of a stainless steel (SUS-32) equipped with an electromagnetic stirrer as a hydrogenation reactor, a sheath for a thermometer, a liquid raw material inlet pipe, a gaseous raw material inlet pipe and a filter were equipped in the autoclave to prepare a continuous hydrogenation reactor. The filter equipped in the reactor was connected with a backwashing device so as to perform a backwashing of a filter medium. A stainless steel 100% woven fabric having 9.5 cm² of a filtering area (manufactured by Nippon Seisen K.K.) was used as the filter medium on the filter.

In the hydrogenation, 150 g of a Raney nickel catalyst (average particle size of 20 to 30μ) and 350 g of ethyl acetate were charged in the hydrogenation reactor and an ethyl acetate solution containing 25 wt.% of polymeric butadiene peroxide was continuously fed at 150° C. of reaction temperature under 100 kg/cm² of hydrogen pressure to carry out the hydrogenation.

The ethyl acetate solution of polymeric butadiene peroxide was fed from a storing tank to the reactor by a high pressure micovolumetric pump at a flow rate of 300 g/hr. while the reaction mixture was discharged from the reactor through the filter to a receiver kept in lower pressure so as to maintain suitable level of the reaction mixture.

The pressure difference between the reactor and the receiver was 5 kg/cm². The reaction mixture was discharged intermittently by opening an electromagnetic valve at the outlet with a timer. When the reaction mixture was discharged to the upper level of the filter in the reactor, hydrogen gas was discharged to raise the pressure in the receiver. The raise of the pressure was detected and the electromagnetic valve at the outlet was closed and the pressure in the receiver was reduced to the normal state.

The hydrogenation was smoothly carried out for a total of 1,000 hours.

The average yields of 1,4-butanediol and 1,2-butanediol based on polymeric butadiene peroxide were respectively 52.9% and 24.9%.

EXAMPLE 2

In accordance with the process of Example 1, an ethyl acetate solution containing 25 wt.% of polymeric butadiene peroxide was hydrogenated.

A filter having a filter medium of stainless steel gauze (filtering area of 10 cm²: 100 mesh cylindrical form) was equipped in the continuous hydrogenation reactor. A nickel catalyst which is resistant to sulfur (manufactured by Nikki Kagaku K.K.) used has an average particle size of 40μ and the formula of 45 to 47% of Ni; 2 to 3% of Cr; 2 to 3% of Cu; 27 to 29% of diatomaceous earth and 4 to 5% of graphite.

In the continuous hydrogenation reactor, 150 g of nickel catalyst and 350 g of ethyl acetate were charged and an ethyl acetate solution containing 25 wt.% of polymeric butadiene peroxide was continuously fed at a flow rate of 300 g/hr. to perform the hydrogenation at 150° C. of reaction temperature under 100 kg/cm² of hydrogen pressure.

The pressure difference between the reactor and the receiver was 10 kg/cm². The reaction mixture was discharged intermittently through the filter in the reactor as that of Example 1.

The hydrogenation was smoothly carried out for a total of 1,000 hours.

The average yields of 1,4-butanediol and 1,2-butanediol based on polymeric butadiene peroxide were respectively 53.0% and 24.8%.

EXAMPLE 3

In accordance with the process of Example 1, an ethyl acetate solution containing 25 wt.% of polymeric butadiene peroxide was hydrogenated.

A filter having a filter medium of a sintered porous metal (filtering area of 9.5 cm$^2$; average pore diameter of 20$\mu$) was equipped in the continuous hydrogenation reactor and 150 g of the nickel catalyst (resistant to sulfur) and 350 g of ethyl acetate were charged and an ethyl acetate solution containing 25% of polymeric butadiene peroxide was continuously fed at a flow rate of 330 g/hr. to perform the hydrogenation at 150° C. of reaction temperature under 100 kg/cm$^2$ of hydrogen pressure.

The pressure difference between the reactor and the receiver was 18 kg/cm$^2$. The reaction mixture was discharged intermittently through the filter in the reactor as that of Example 1.

When the hydrogenation was continued for 700 hours, the discharge rate of the reaction mixture was reduced. Accordingly, the filter medium was backwashed with ethyl acetate and the hydrogenation was further continued for 300 hours (total: 1,000 hours).

The average yields of 1,4-butanediol and 1,2-butanediol based on polymeric butadiene peroxide were respectively 52.8% and 24.8%.

EXAMPLE 4

In a continuous hydrogenation reactor equipped with a filter having a filter medium of a stainless steel woven fabric (filtering area of 10 cm$^2$: sheathless and cylindrical form) inside, 70 g of Raney nickel catalyst, 300 g of water were charged and and aqueous solution containing 50 wt.% of glucose was continuously fed at a flow rate of 400 g/hr. to perform the hydrogenation at 150° C. of reaction temperature under 130 kg/cm$^2$ of hydrogen pressure.

The pressure difference between the reactor and the receiver was 16 kg/cm$^2$. The reaction mixture was discharged intermittently through the filter in the reactor as that of Example 1.

The hydrogenation was smoothly carried out for a total of 1,000 hours.

The yield of sorbitol was 94.7% in constant.

What is claimed is:

1. A process of reaction in a suspended catalyst system which comprises continuously reacting an organic compound in the presence of a suspended solid catalyst in a liquid phase in a reactor equipped with a filter disposed in the reactor for separating the suspended catalyst in the reactor from the reaction product as it leaves the reactor to pass to a reaction product receiver whereby the reaction and separation of the suspended catalyst are continuously performed in the reactor, backwashing the reactor when the filtering speed is reduced below a predetermined value, and resuming the continuous reaction.

2. A process according to claim 1 wherein a ratio of the suspended catalyst to a total mixture in the reactor is more than 3 wt.%.

3. A process according to claim 1 wherein the filter has a flexible filter medium.

4. A process according to claim 2 wherein solid catalyst, liquid and gas are contacted and the pressure in the filter is higher than that of the receiver at a difference of less than 35 kg/cm$^2$.

5. A process according to claim 1 wherein the filter has a filter medium made of steel woven fabric, gauze, screen or porous plate.

6. A process according to claim 4 wherein the filter is disposed in the reactor at a level of the mixture so as to maintain the lowest level in a discharge of the reaction mixture in a reaction with a gaseous reagent.

7. A process according to claim 6 wherein the pressure in the reaction is higher than 1 kg/cm$^2$.

8. A process according to claim 6, wherein the reaction is a hydrogenation or an oxidation in the presence of a suspended solid catalyst and a gaseous reagent.

9. A process according to claim 4 wherein the reaction is a hydrogenation with hydrogen in the presence of a suspended hydrogenation catalyst.

10. A process according to claim 9 wherein the organic compound is organic peroxide and the main product is mono- or polyhydric alcohol.

11. A process according to claim 4 wherein the reaction is an oxidation with oxygen in the presence of a suspended oxidation catalyst.

12. A process according to claim 7 wherein the reaction is a hydrogenation of polymeric butadiene peroxide with hydrogen in the presence of nickel catalyst to produce butanediol.

13. A process according to claim 12 wherein exiting hydrogen gas and outflowing liquid reaction mixture are discharged to the receiver, and wherein when the pressure in the receiver rises above a predetermined value, discharge to the receiver is interrupted until the pressure therein falls.

* * * * *